United States Patent [19]

Hütsch et al.

[11] Patent Number: 4,726,678
[45] Date of Patent: Feb. 23, 1988

[54] RECEPTACLE FOR FLAMELESS ATOMIC ABSORPTION SPECTROSCOPY

[75] Inventors: Bruno Hütsch, Bonn, Fed. Rep. of Germany; Wolfgang Frech, Umea, Sweden

[73] Assignee: Ringsdorff-Werke GmbH, Bonn, Fed. Rep. of Germany

[21] Appl. No.: 912,928

[22] Filed: Sep. 26, 1986

[30] Foreign Application Priority Data

Sep. 27, 1985 [DE] Fed. Rep. of Germany ....... 3534417

[51] Int. Cl.4 .......................................... G01N 21/16
[52] U.S. Cl. ..................... 356/244; 356/312
[58] Field of Search .................... 356/244, 246, 312

[56] References Cited

U.S. PATENT DOCUMENTS 4,204,769  5/1980  Lersmacher et al. .......... 356/312 X
4,407,582  10/1983  Woodriff ............................ 356/312

FOREIGN PATENT DOCUMENTS 3140458  4/1983  Fed. Rep. of Germany .

OTHER PUBLICATIONS

Spectrochimica Acta, 37B, 1021, 1982.

Primary Examiner—Eugene R. LaRoche
Assistant Examiner—David Mis
Attorney, Agent, or Firm—Herbert L. Lerner; Laurence A. Greenberg

[57] ABSTRACT

Unitary receptacle and contact pieces for vaporization and spectroscopic analysis of an analysis sample. Receptacle means are incorporated in the receptacle reception of the sample. The contact pieces are formed integrally with the receptacle for connection of the reception means to an electrical supply unit to enable the sample to be heated. The reception means may constitute a bore in the receptacle, a cup for containing an analysis sample engageable in the bore and additional contact pieces formed integrally with the cup for connection of the cup with a current supply unit therefor.

8 Claims, 10 Drawing Figures

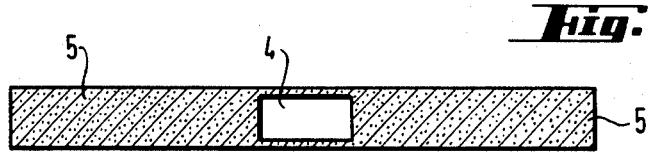
Fig. 2b
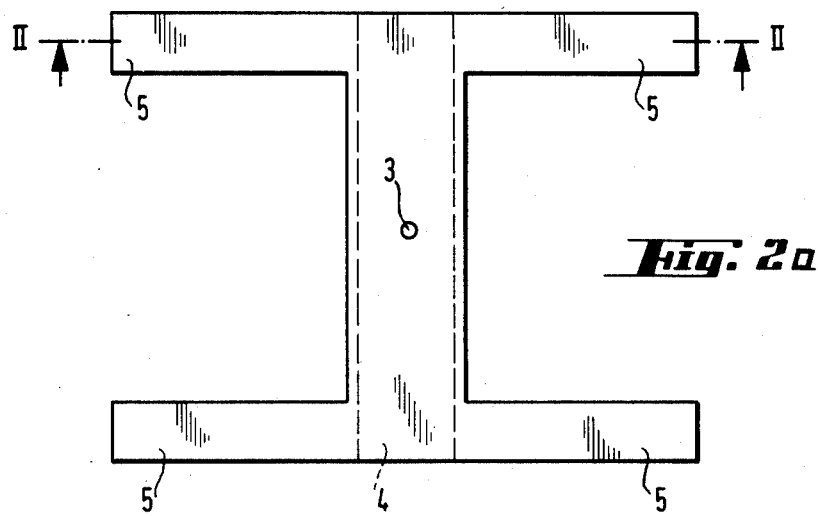
Fig. 2a
Fig. 3
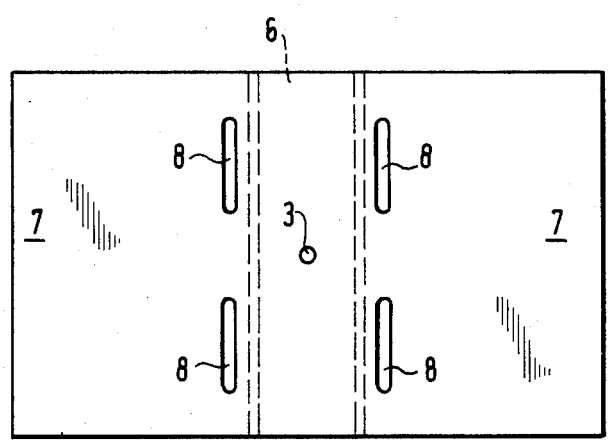

RECEPTACLE FOR FLAMELESS ATOMIC ABSORPTION SPECTROSCOPY

BACKGROUND OF THE INVENTION

1. Field of the Invention

This invention relates to a receptacle for the reception, vaporization and atomization of analysis samples for atomic absorption spectroscopy.

2. Description of the Prior Art

In flameless atomic absorption spectroscopy, the analysis sample introduced for example through a lateral opening into a tubularly extended receptacle is evaporated and yields an "atom cloud" consisting essentially of free atoms which is irradiated in the direction of the tube axis with a measured light beam containing resonance lines of the element which is sought. The temperatures required for drying, ashing, vaporization and atomization are produced by Joule's law heating of the receptacle which consists of a temperature resistant conductor, preferably made of graphite or other carbon types of material, such as pyrographite, vitreous carbon, and as a rule is connected via contact pieces with an electrical supply arrangement. The factors determining precision of analysis are, inter alia, the residence time of the vaporized analysis substance in the receptacle, the atomization time and the ratio of the two measurements. Numerous proposals have been made for shortening the time span necessary for the atomization, above all by higher rate of heating. For example, it is known, to reduce the losses caused by radiation, which losses limit the heating rate, by encasing the receptacle with jacket-like insulating bodies. Another proposal was to restrict the current flow through a layered construction to a narrow zone extending from the inner wall (German Offenlegungsschrift No. 31 40 458). Another essential requirement for the precision of analysis is a small temperature fluctuation over the volume of the receptacle. Especially harmful are, in this connection, matrix effects which achieve reversal to reactions of the desired elements with other components of the analysis sample and formation of compounds which are resistant in zones of lower temperature. At the least, one can reduce, in part, the harmful effects by additions of specific reagents or calibrating substances and even by selective evaporation. The cost of this, for its part, is large, without the reliability of analysis being essentially increased.

Finally, it is known from U.S. patent specification No. 4,407,582 to heat the tubular ends of receptacles alone by direct current passage alone and to heat the center thereof, proceeding from the ends of the receptacle by means of heat conduction and radiation. The energy supplied naturally must suffice for the decomposition and atomization of the analysis sample. No temperature sinks are to exist in the direction of the ends of the receptacle. Electrical energy is supplied to the ends of the receptacle over Y-shaped contact pieces or a slotted casing which connects to special shoulders of the receptacle ends.

The matrix effect is clearly less with these constructional forms than with tubular receptacles with central current supply. A disadvantage of the arrangement is the restriction of the rate of heating as a result of the permitted current densities of the contact pieces. The receptacle ends can become exposed, without being destroyed, by evaporation of the carbon, peeling off of graphite flakes or the formation of cracks. The supply of sufficient energy to the core zone by Joulean heat and irradiation for the atomization of all test substances and the suppression of the matrix effect are therefore not always successful. Even with normal electrical current density, the contacts are strongly stressed and a rapid wearing may be difficult to avoid.

The disadvantages of this solution are to a large extent avoided with an arrangement in which different heating circuits are provided for the tubular graphite receptacles and for a special cup for the reception of the substance to be analyzed. The receptacle is initially heated up to the predetermined temperature and after reaching this temperature the cup inserted in an opening in the receptacle is heated with the substance to be analyzed with a high rate of heating to the atomization temperature (Spectrochimica Acta 37B, 1021, 1982). Within one to two seconds, temperatures of about 2700° C. are achieved and a constancy of temperature with respect to both space and time, improving the precision of analysis, is achieved. Even with this constructional arrangement, the alteration with time of the contact positions between receptacles or cups and the graphite rods serving for the supply of current is technically not satisfactory. It is especially difficult reproducibly to attach the contact rods. Different contact resistances exist too as a result of variations in the shape of the contact partners as a consequence of steep variations in temperature. The described effects reduce the operating life of the system which includes the receptacle and make routine analyses difficult.

SUMMARY OF THE INVENTION

An object of the invention is to provide a receptacle and contact pieces for atomic absorption spectroscopy in which the spread of contact resistances between receptacle and contact pieces is minimized, and also an increase in the operating life of the receptacle and contact pieces.

With the foregoing and other objects in view, there is provided in accordance with the invention a unitary receptacle and contact pieces comprising a receptacle incorporating means for the reception of an analysis sample for vaporization and spectroscopic analysis therein, and contact pieces formed integrally with the receptacle for connection of the reception means to an electrical supply unit to enable the sample to be heated.

Other features which are considered as characteristic for the invention are set forth in the appended claims.

Although the invention is illustrated and described herein as embodied in a receptacle for flameless atomic absorption spectroscopy, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings, in which:

FIG. 1b is a section through the receptacle of FIG. 1a taken along line I—I of FIG. 1a;

FIG. 2a is a plan view of another receptacle, with shortened contact pieces;

FIG. 2b is a section through the receptacle of FIG. 2a taken along line II—II of FIG. 2a;

FIG. 3 is a plan view of a receptacle with slotted contact pieces;

DESCRIPTION OF THE PREFERRED EMBODIMENTS

Figure 1B:
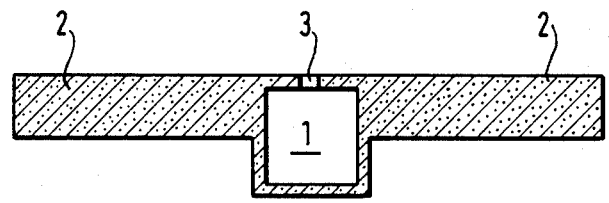

According to the invention, there is provided a receptacle incorporating means for the reception of analysis samples for vaporization and spectroscopic analysis while therein, the receptacle being formed integrally with contact pieces for connection of the reception means to an electrical supply unit to enable the samples to be heated by Joule's law effect.

With a unitary receptacle and contact pieces embodying this invention, there is a reduction of the spread of contact resistances between receptacle and contact pieces and an increase in the operating life of receptacles and contact pieces. Moreover, the time periods for the setting up of the temperature equilibrium are reduced.

Receptacles according to the invention are bodies extended in the direction of the measuring radiation with circular, square or any other suitable cross-section, from which at least two contact bodies run, extending from the receptacle surface as a continuation of the receptacle structure. As a result of the unity of the receptacle and contact bodies, there are no contact resistances and, accordingly, there is not excessive heating of the contacts nor pitting as a result of arcing and, likewise, no mechanical stresses induced as a result of differing thermal expansion coefficients on heating. The ends of the wing-type contact pieces are connected at a distance from the receptacle surface with the electric current supply unit. Because of the separation of the ends of the contacts from the surface of the receptacle, the thermal loading of the contacts may be readily reduced by insulation, radiation shields, cooling or other known measures. The operating life of the "cold" contact positions is practically unlimited.

The receptacle is preferably provided with a recess in which the essentially hollow cylindrical or boat-shaped cup filled with analysis substance is engaged. At least two contact pieces also preferably extend from the wall of the cup, which pieces are connected at a spacing from the wall with a second current supply unit. Damaging of the cup by overheating in the contact, cratering by arcing and similar defects are voided by the contact positions now being in regions of lower temperature and the service time of the total system formed from receptacle and cup is correspondingly prolonged.

Receptacles and evaporation cups comprised thereby are desirably made of the purest graphite, pyrographite, vitreous carbon or another type of carbon with a low ash content. They are produced by die pressing or extrusion pressing of carbon or graphite powders which are treated with a binder. The shaped bodies are then heated for carbonization of the binder to about 2800° to 3000° C., subjected to purification and, if necessary, brought to the final form by machine working. Such working is usually required for production of complicated shapes.

According to a preferred embodiment of the invention, the contact pieces forming a unit with the receptacle extend over the entire length of the receptacle. (By length is meant the maximum dimension parallel to the longitudinal axis of that portion of the receptacle which contains the analysis sample, i.e. the length of the receptacle 1 in FIG. 1a would extend from the top to the bottom of the receptacle). With this constructional form, the entire receptacle is heated uniformly and there are practically no axial temperature gradients. For the reduction of heat dissipation, in another preferred constructional form, the contact pieces are provided with apertures therethrough which shorten their cross-section. Preferably the apertures extend in the direction of the receptacle length dimension. By splitting-up the contact pieces into a plurality of parallel segments or by a variation in their thickness, one may, in a simple way, match the electrical resistance of the unit formed from receptacle and contact pieces to the output of a given electrical current supply unit to produce temperature profiles within the receptacle for special analysis conditions. The apertures are worked into the contact pieces as appropriate by boring, sawing or milling.

For analysis, the analysis sample is disposed in a boat in the receptacle, being injected into the receptacle through a special opening, after preheating of the receptacle, or as appropriate is introduced in a small cup, which engages in a bore of the receptacle. The receptacle and the cup are connected each with a current supply arrangement independent of one another and each can be heated independently with predetermined rates of heating advantageous for the analysis sample. On account of the unity of receptacle and contact pieces, the high heating speed does not result in the damaging or even the destruction of the receptacle by overheating at the contact positions or other contact deficiencies and in a short period of time one achieves a constant temperature distribution in the receptacle.

For a better understanding of the invention and to show how the same can be carried into effect, reference will now be made, by way of example only, to the accompanying drawings.

Figure 1A:
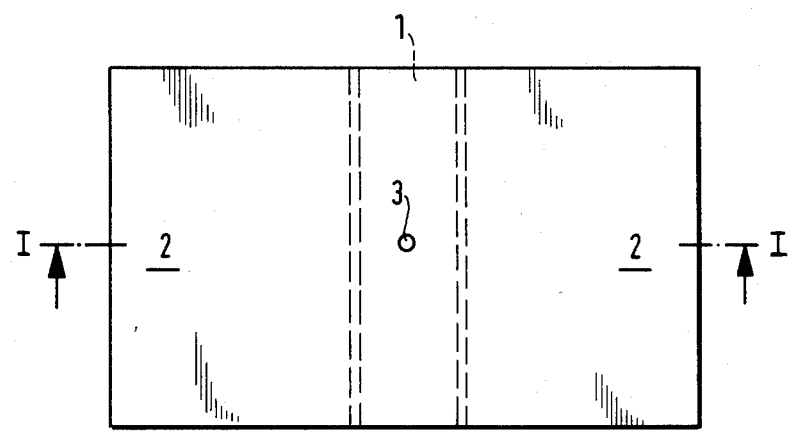
FIG. 1a is a plan view of a receptacle according to the invention with contact pieces extending thereacross.

In the construction according to FIGS. 1a and 1b, a receptacle 1 and contact pieces 2 extending over the entire length of the receptacle form one unit. A bore 3 is provided for the introduction of an analysis sample. Not shown in the drawing are the connection of the contact pieces with an electrical supply unit and means for cooling and for providing thermal insulation of the junction positions. Such connection and means are conventional and known to the man skilled in the art. The construction makes possible a rapid heating up of the receptacle without the formation of an axial temperature gradient.

In FIGS. 2a and 2b is shown a variant of the receptacle of FIGS. 1a and 1b in which a receptacle 4 has shortened contact pieces 5. The receptacle ends are heated directly in this construction, the central region being heated indirectly by radiation and thermal conduction.

FIG. 3 shows a receptacle 6 whose contact piece 7 is provided with slots 8. The slots serve predominantly for reduction of heat flow from the receptacle to the ends of the connection pieces and for matching of the electrical resistance to the output of the electrical supply unit.

Figure 4:
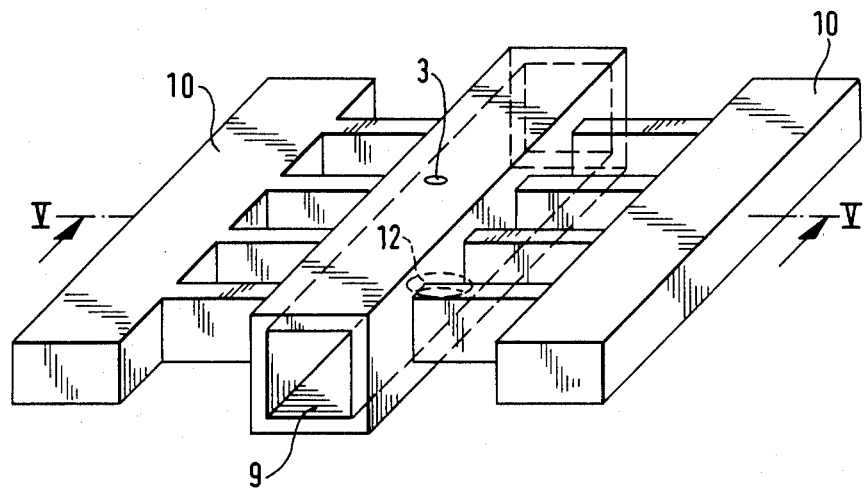
FIG. 4 is a perspective view of a receptacle with apertured contact pieces.
Figure 5:
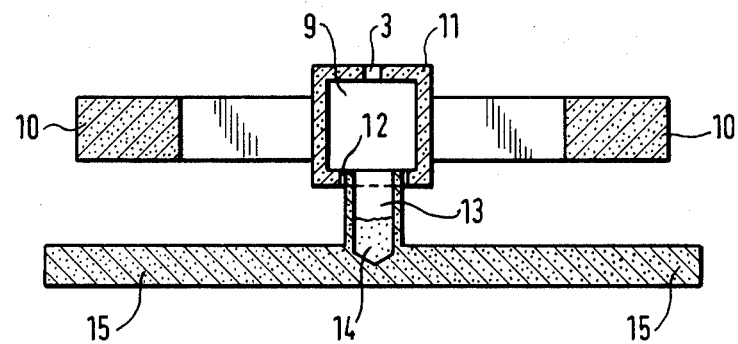
FIG. 5 is a vertical section through the receptacle of FIG. 4, the receptacle including a cup engaged therewith.
Figure 6A:
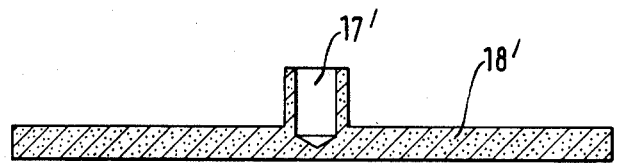
FIGS. 6a–6c are vertical sections through cups with contact pieces.
Figure 6B:
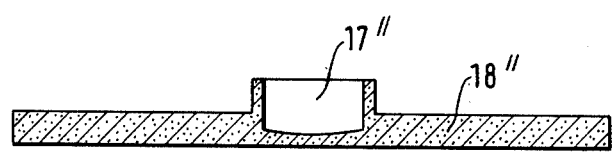
Figure 6C:
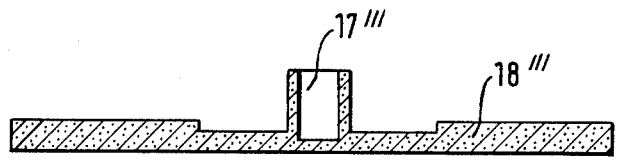

In FIG. 4, there is shown in perspective view a receptacle 9 with multiple apertured contact pieces 10. This construction is especially suited for setting of predetermined temperature profiles. The receptacle is provided with a bore 12 in which is engaged a cup 13 which latter contains an analysis sample 14 (see FIG. 5). The cup 13 forms a unit with contact pieces 15 which are connected with a current supply unit which are not shown in the drawing. The contact pieces 10 which form a unit with the receptacle 11 are connected with a special current supply unit. In FIG. 6 a–c are shown a few units consisting of cups 17′, 17″ and 17‴ and contact pieces 18′, 18″, and 18‴ of a form determined in experiments to be advantageous.

Receptacle and cup can advantageously also be used as supports for analysis samples with other spectroscopic processes, for example for emission or fluorescent spectroanalyses.

The foregoing is a description corresponding, in substance, to German application No. P 35 34 417.2, dated Sept. 27, 1985, international priority of which is being claimed for the instant application and which is hereby made part of this application. Any material discrepancies between the foregoing specification and the specification of the aforementioned corresponding German application are to be resolved in favor of the latter.

We claim:

1. Unitary receptacle and contact pieces comprising a receptacle incorporating means for the reception of an analysis sample for vaporization and spectroscopic analysis therein, and contact pieces formed integrally with the receptacle for connection of the reception means to an electrical supply unit to enable the sample to be heated.

2. Unitary receptacle and contact pieces according to claim 1, wherein the receptacle is a tubularly extended receptacle, and wherein the contact pieces extend over the whole length of the tube.

3. Unitary receptacle and contact pieces according to claim 1, wherein the contact pieces are provided with the apertures which reduce the cross-section thereof.

4. Unitary receptacle and contact pieces according to claim 2, wherein the contact pieces are provided with the apertures which reduce the cross-section thereof.

5. Unitary receptacle and contact pieces according to claim 4, wherein the apertures are a plurality of slots which extend parallel to the tube.

6. Unitary receptacle and contact pieces according to claim 1, wherein the reception means comprises a bore in the receptacle, a cup for containing an analysis sample engageable in the bore and additional contact pieces formed integrally with the cup for connection of the cup with a current supply unit therefor.

7. Unitary receptacle and contact pieces according to claim 1, wherein the unitary receptacle and contact pieces are formed of carbon or graphite.

8. Unitary receptacle and contact pieces according to claim 6, wherein the unitary receptacle and contact pieces as well as the cup and its integrally formed contact pieces are formed of carbon or graphite.

* * * * *